United States Patent [19]

Williams et al.

[11] 4,446,568
[45] May 1, 1984

[54] VERSATILE FOCUSING RADIATION ANALYZER

[75] Inventors: Arthur R. Williams; William L. Johnson, both of Pasadena, Calif.

[73] Assignee: California Institute of Technology, Pasadena, Calif.

[21] Appl. No.: 270,968

[22] Filed: Jun. 5, 1981

[51] Int. Cl.³ .................. G01N 23/02; G01N 23/20; G01N 23/22
[52] U.S. Cl. .................................. 378/3; 378/83; 378/84; 378/85
[58] Field of Search ............ 378/3, 84, 82, 79, 81, 378/83, 85, 49

[56] References Cited

U.S. PATENT DOCUMENTS

| | | | |
|---|---|---|---|
| 2,898,469 | 8/1959 | Rose | 378/83 |
| 2,951,157 | 8/1970 | Haine et al. | 378/49 |
| 3,073,952 | 1/1963 | Rose | 378/49 |
| 4,078,175 | 3/1978 | Fletcher et al. | 378/79 |

Primary Examiner—Alfred E. Smith
Assistant Examiner—T. N. Grigsby
Attorney, Agent, or Firm—Freilich, Hornbaker, Rosen & Fernandez

[57] ABSTRACT

A versatile focusing radiation analyzer for EXAFS, fluorescence EXAFS, Raman or modified Compton scattering, diffraction, Rayleigh scattering and other experiments is comprised of a concave focusing element (10) placed at the end of a central arm (11) pivoted at the center (24) of a circle (21). Side arms (12, 13) are also pivoted at the center (24). A platform (17) supports an X-ray source (50, 61, 66) or a sample (16) at the end of one side arm (12) while a platform (23) supports a detector (22, 63, 66), sample (51) and detector (52) or Mössbauer source (80). Constraining bars (14, 15) attached to the side arms and to a slide (29) in a slot (30) cause one side arm (13) to maintain an angle ($\theta$) with the center arm equal to the angle of the other side arm (12) with the center arm as the center arm is driven relative to that side arm by suitable means (25–28). Rods (31, 32) or belts (36, 38) with pulleys (35, 37) maintain the optical axis of the elements on the platforms (17, 23) directed to the center of the focusing element (10) as the angle ($\theta$) is varied. The focusing element (10) may be a single crystal bent and polished to a Johanssen focusing configuration, or a sample bent to the same configuration, depending on the experiment. A small focusing crystal (20) may be used to select one of the characteristic lines of the X-ray source (19). The acquisition time of a complete scan of the angle $\theta$ may be reduced without increasing the source intensity or sacrificing resolution due to the focusing geometry of the concave element.

12 Claims, 13 Drawing Figures

VERSATILE FOCUSING RADIATION ANALYZER

ORIGIN OF INVENTION

The invention described herein resulted from Contract DE-AC03-76ER00822 between the U.S. Department of Energy and California Institute of Technology.

FIELD OF THE INVENTION

The invention relates to a radiation analyzer, and more particularly to an instrument for high resolution X-ray energy analysis, such as for absorption, anomalous dispersion, and X-ray Raman effect studies, and for higher acquisition rate diffraction studies and Rayleigh scattering studies using Mössbauer source gamma rays, to obtain specific structural information of materials.

BACKGROUND OF THE INVENTION

A variety of new techniques have recently been developed for the study of atomic scale structure of solids. In addition to conventional diffraction, several new methods of utilizing X-ray radiation to obtain structural information have recently been explored. The fine structure observed near the X-ray absorption edge of an atom in a solid is the basis for one such technique commonly referred to by the acronym EXAFS (Extended X-ray Absorption Fine Structure). This technique gives detailed information concerning the local environment of a specific atomic species.

Recent studies and theoretical calculation suggest that a corresponding fine structure should occur when an X-ray is Compton scattered by a bound electron which is subsequently excited to a higher unoccupied energy level. This scattering can be called either Raman or modified Compton scattering (MCS). By carrying out an energy dispersive analysis of X-rays so scattered, it should be possible to obtain information identical to that obtained by EXAFS. The MCS technique would be ideally suited for studying light elements where EXAFS experiments are generally difficult to carry out.

Another type of X-ray experiment involves the use of anomalous X-ray dispersion to extend conventional diffraction studies to multicomponent materials. By using this effect, one can combine the information obtained in two experiments utilizing different characteristic X-ray radiations to derive the atomic environment of each separate component in the material.

Scientists are particularly interested in understanding the properties of amorphous (noncrystalline) materials. Both of the techniques described above would provide precisely the type of structural information required to understand atomic arrangements in such materials. This information in turn can be used to understand the macroscopic properties of noncrystalline solids.

X-ray and neutron diffraction techniques have always offered the most straightforward method of studying the structure of materials. For multicomponent alloys, however, specific quantitative information on the individual atomic species is in general very difficult to extract from these experiments for a number of reasons. A strong effort is therefore being made by many researchers to take advantage of several relatively new techniques, such as EXAFS, anomalous dispersion studies, and combined neutron and X-ray diffraction studies, to obtain much more specific statistical structural information. What is desired for this effort is a high resolution, high acquisition rate, X-ray instrument which can be used in several different configurations.

The typical arrangement of apparatus used in a study of Compton scattered X-rays utilizes two flat crystals. Experiments using a double-crystal spectrometer have been reported in the literature. K. Das Gupta, *Phys. Rev. Lett.*, 21, 338 (1964) is selected as representative because it best illustrates the geometry, and the problem of making fine coordinated adjustments in the angular positions of the crystals. A more complex triple-crystal geometry was used in an experiment reported by N. G. Alexandropoulos and G. G. Cohen, *Phys. Rev.*, 187, 455 (1969). A single spectrometer arrangement has also been used with two slit tubes in an experiment reported by K. Das Gupta, *Phys. Rev.*, 128, 2181 (1962). It required three coordinated adjustments: (1) the sample orientation with respect to the X-ray beam, (2) the position of a slit tube in the path of the sample reflected beam so that the mean scattering angle $\phi_m$ is known, and (3) the angular position of a second slit tube so that the rays scattered at $\phi_m$ make the proper Bragg angle through a quartz crystal. A second, more complex single-crystal method is also illustrated by K. Das Gupta. These two methods are variants of the double-crystal spectrometer arrangement which has been in use since at least 1930. See J. A. Bearden, *Phys. Rev.*, 36, 791 (1930), N. S. Gingrich, *Phys. Rev.*, 36, 1050 (1930), and W. M. DuMond and H. A. Kirkpatrick, *Phys. Rev.*, 37, 136 (1931).

What is needed is a high resolution energy analyzer requiring only one manual adjustment to quickly carry out experiments to measure modified Compton scattering in solids and to study the X-ray absorption edge and the associated extended X-ray absorption fine structure (EXAFS). From the Compton scattering data, it is possible to extract information similar but complementary to that available from conventional EXAFS experiments. To study the X-ray absorption edge and the associated EXAFS, A. A. Bahgat and K. Das Gupta devised a single-crystal geometry as reported in *Rev. Sci Instrum*, 50, 1020 (1979). A microfocus X-ray tube with a small focal spot is positioned on the circumference of a circle centered on the single Si crystal such that the entire crystal is exposed to the X-ray beam passing through a sample. A film or moving detector on an arc (segment of a circle centered on the virtual image point of the crystal reflected energy) yields the absorption spectrum of the sample. However, this relatively simple arrangement lacks the desired versatility of an instrument capable of also carrying out Raman or modified Compton scattering experiments, and also requires the use of some type of position sensitive detector or a scanning mechanism.

A major limitation inherent in EXAFS studies has been sufficient intensity or radiation flux. As reported by P. Eisenberger and B. M. Kincaid, *Science*, 200, 1441 (1978), the increase in flux of approximately $10^5$ to $10^6$ provided by the Stanford synchrotron has vastly expanded the use of EXAFS in the study of materials. The authors summarize the current quantitative understanding of EXAFS, and describe how measurements are made using the Stanford synchrotron. Unfortunately, the availability of the Stanford synchrotron for EXAFS studies of materials is limited. More EXAFS studies could be carried out if there were available an instrument of high flux intensity that could be placed in the laboratory of virtually every scientist interested in carrying out EXAFS experiments as and when needed. At least one such laboratory instrument has been developed, as reported by G. S. Knapp, H. Chen and T. E. Klippert, *Rev. Sci. Instrum.*, 49, 1658 (1978). It uses a Johanssen cut Germanium crystal as a focusing monochromator to increase flux intensity. Both the radiation source and the detector are positioned outside the Rowland circle of the Johanssen cut crystal. The sample is then placed in the beam between the crystal and the detector. The arrangement was implemented using a standard General Electric XRD-5 horizontal diffractometer, with the result that a complex alignment procedure is required. The procedure outlined requires four physical elements to be aligned. Although complete alignment procedures are required only for initially setting up an experiment, many adjustments are still required for each different measurement over the entire spectrum, and a microprocessor is necessary to drive the three independent positioning motors which are required.

OBJECTS AND SUMMARY OF THE INVENTION

In accordance with the present invention, a concave element is supported by one arm pivoted at the center of a circle. The surface of the concave element lies on the circumference of the circle. Also provided at the center of the circle are two arms, one on each side of the arm on which the concave element is mounted. Mounted on one side arm at the same radius as the concave element on the central arm is a means for directing a beam of radiation from a virtual point source to the concave element. Mounted on the other side arm of the central arm is a means for receiving a focused beam of radiation from the concave element. Also provided are means for maintaining the angle between the central arm and each side arm equal as the angle between one arm and the central arm is varied, and means for simultaneously maintaining the beam axis of the virtual point source directed to the center of the concave element and maintaining the beam axis of the receiving means directed to the center of the concave element as the angle of the central arm relative to one side arm is varied, and the other side arm is caused to maintain the same angle with the central arm.

The concave element may be a polished single crystal carefully bent for focusing radiation from the virtual point or line source on one side arm to a point on the receiving means on the other side arm with those points at the same radius as the concave element on the central arm. The receiving means may be a detector having a slit at that radius, with a sample in front of it, as for EXAFS studies, or without a sample in front of it, as for Raman experiments, using an X-ray source. In the case of Raman experiments, the source may be comprised of an X-ray source and a second single crystal carefully bent and polished for focusing radiation from the X-ray source on one side of the crystal to the point on the side arm at the circumference of the circle. There a sample reflects radiation to the focusing crystal on the central arm. The positions of the X-ray source and second crystal may be varied to select a particular X-ray line using some means for maintaining the X-ray source and second crystal on a circle in a manner similar to the way the receiving means and main focusing crystal are positioned relative to the virtual point source. An alternative arrangement, for fluorescence EXAFS studies, is to position a sample at the focusing point of the main crystal, and to place a detector in a position to detect radiation reflected from the sample.

The concave element may also be a sample carefully bent for focusing radiation from the virtual point source on one side arm to a point on the receiving means at the same radius as the concave element on the central arm for diffraction studies since diffraction from the bent sample always occur at well defined diffraction angles, $2\theta$. As in the arrangement for Raman experiments, an X-ray source and second crystal may be used as the means for providing a virtual point source to enable the X-ray line to be used in the diffraction experiment. An alternative is to replace the X-ray source with a Mössbauer gamma ray source, and to place behind the slit of the detector a matched absorber with oscillating means for shifting the position of the absorber back and forth in the direction of radiation at high speed. Measurement of inelastically scattered gamma rays is made when the absorber is at rest and measurement of the total (elastic plus inelastic) scattering cross section is made when the absorber is moving.

The novel features that are considered characteristic of this invention are set forth with particularity in the appended claims. The invention will best be understood from the following description when read in connection with the accompanying drawings.

DETAILED DESCRIPTION OF PREFERRED EMBODIMENTS

Figure 1:
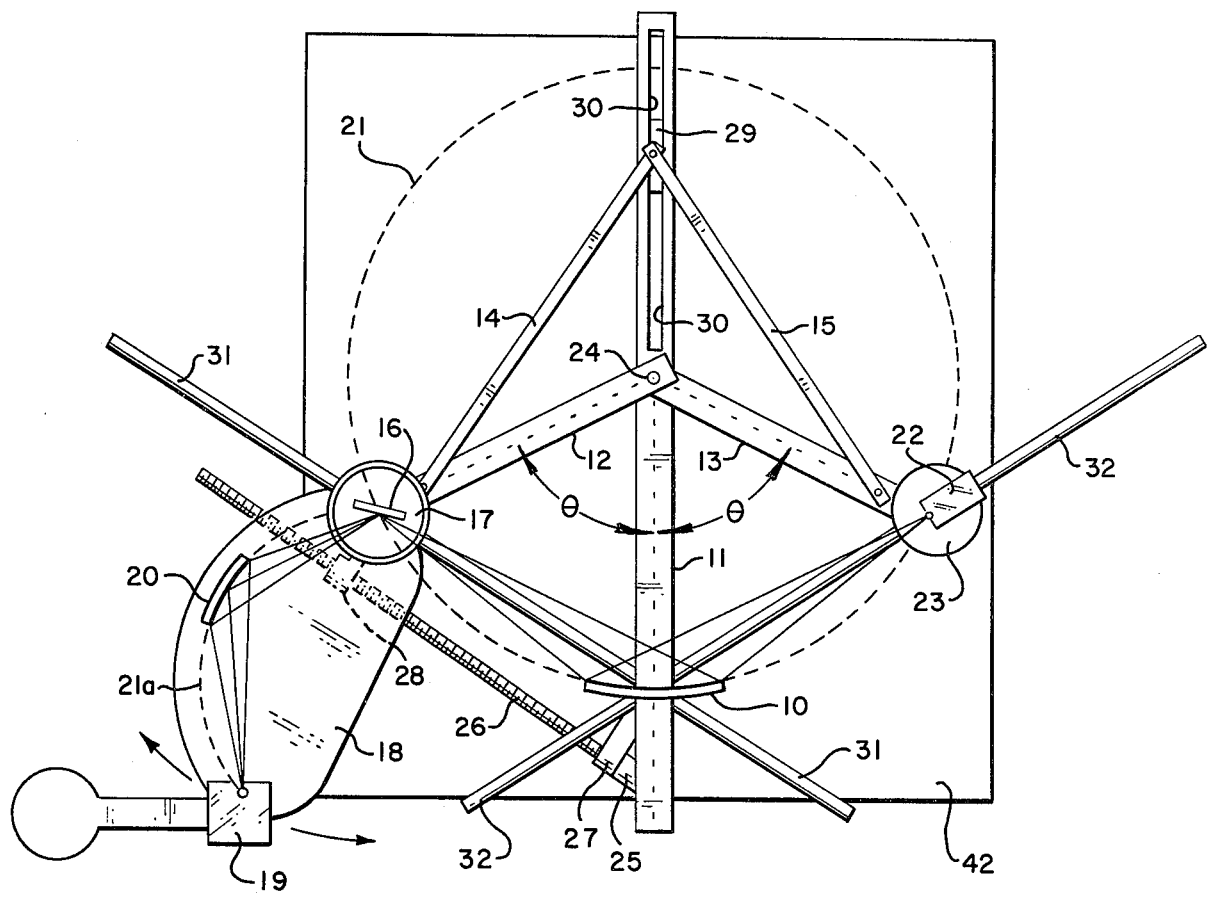
FIG. 1 is a schematic diagram of one embodiment of the invention in a configuration for a Raman type experiment.

Referring now to FIG. 1 of the drawings, a high resolution energy analyzer is comprised of a concave focusing element 10 and high precision apparatus having three arms 11, 12 and 13, and constraining bars 14 and 15, in a configuration to carry out experiments to measure the Raman or modified Compton scattering of X-rays by light elements in solids. From this data, information similar but complementary to that available from the conventional EXAFS experiment may be extracted. As will be noted hereinafter, the energy analyzer may also be used in the EXAFS and other modes by simple modifications.

The central elements of this new and improved energy analyzer is the large (0.787"×5") oriented germanium single crystal 10 which is carefully bent and polished to a Johanssen focusing configuration and mounted on the central arm 11 of the apparatus. This will perform as an efficient, high resolution X-ray energy analyzer with which it will be possible to obtain accurate energy profiles of the X-ray intensity scattered from a sample 16 of interest mounted on a platform 17. Pivoted directly under the face of the sample at its center is a plate 18 which supports a horizontally mounted X-ray tube 19 and a monochromating crystal 20 which is a small (0.787"×2") oriented germanium single crystal carefully bent and polished to a Johanssen focusing configuration.

The plate 18 is initially adjusted for the desired angle of incidence on the face of the sample 16 while the sample platform 17 is initially adjusted to direct the axis of the reflected beam to the center of the energy analyzing crystal 10 for the selected angle of incidence. It should be noted that the surface of the concave focusing element 10 lies on the circumference of a circle 21. A photodetector 22 on a platform 23 is fixed with its optical axis aligned with the axis of the beam reflected by the Johanssen crystal 10. The sample 16 and photodetector 22 are carried on the side arms 12 and 13, respectively, at the same radial distance from a pivot 24 as the radius of the circle 21 of the energy analyzing crystal 10.

The monochromating crystal 20 selects one of the characteristic lines (e.g., $K_{\alpha 1}$, $K_{\beta 1}$) from the X-ray source 19 to be incident on the sample 16 by adjustment of the relative positions of the source 19 and monochromating crystal 20 to the sample 16 on a circle 21a of the same radius as the curvature of the monochromating crystal. Once this adjustment is made, the plate 18 is locked onto the platform 17 so that the relative positions of the X-ray source 19 and monochromating crystal 20 to the sample remain fixed for the selected characteristic line while the platform 17 pivots as the angles between the central arm 11 and the side arms 12 and 13 are varied equally as the energy analyzer 10 is caused to sweep in energies below $E_{CuK\alpha}$-$E_{K\text{-}edge\ sample}$ for Raman fine structure. Controlled sweeping is carried out by, for example, energizing a stepping motor 25 which turns a threaded shaft 26.

At the drive end of the shaft 26, a bracket 27 pivotally secures the motor 25 and shaft 26 to the central arm 11. At the other end of the shaft 26, a bracket 28 is pivotally secured to the arm 12. The bracket 28 is threaded so that as the drive shaft 26 turns in one direction or the other, the bracket 28 is driven toward or away from the bracket 27, thus changing the angle $\theta$ between the arms 11 and 12. The arm 13 is caused to move in a complementary way to maintain the angle between the arm 13 and the central arm 11 equal to the angle between the arm 12 and the central arm 11 by the constraining bars 14 and 15 pivoted at one end on a slide 29 locked in a slot 30 on the central arm 11 extending behind the pivot 24.

An alternative drive may be a step motor for turning a friction wheel supporting the free end of the central arm 11, or a pinion engaging a circular rack. Each turn, or fraction of a turn of the friction wheel or pinion will then pivot the central arm 11 relative to the side arm 12 by some very small angle which may be measured by counting the turns of the wheel or pinion in degrees of rotation for very high resolution. Another arrangement would be to drive the slide 29 in the slot 30, but the high precision desired would be difficult to achieve with that arrangement.

Figure 2:
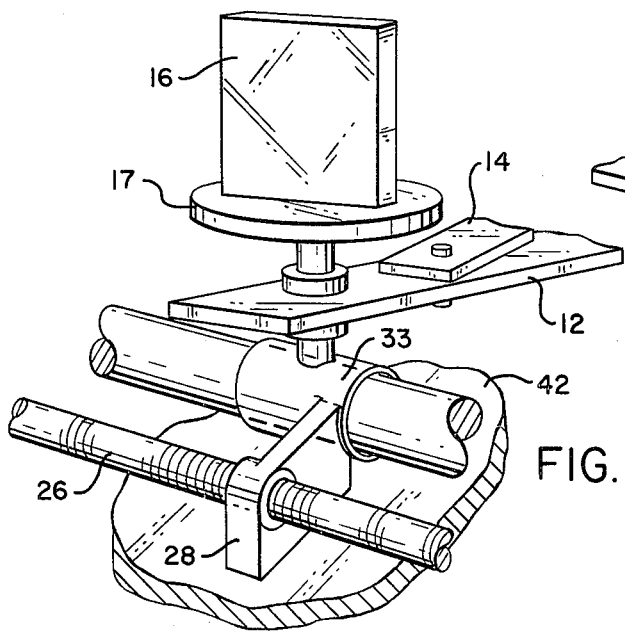
FIG. 2 illustrates details of construction at one end of a side arm in the embodiment of FIG. 1
Figure 3:
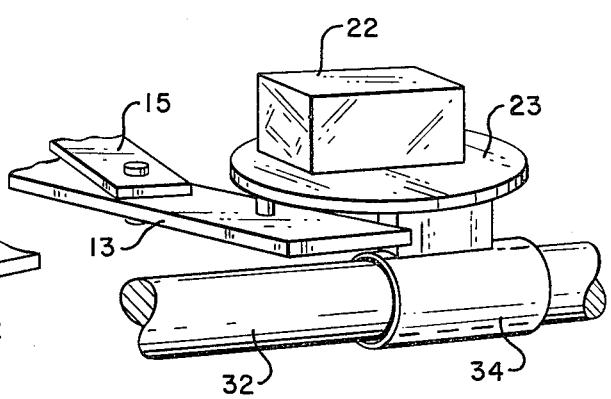
FIG. 3 illustrates details of construction at one end of the other side arm in the embodiment of FIG. 1.

As the angle $\theta$ is varied by some increment, $\Delta\theta$, the platforms 17 and 23 for the sample 16 and detector 22 must be turned by half the increment, $\frac{1}{2}\Delta\theta$, to maintain the beam axes between the sample 16 and the energy analyzing crystal 10, and between the detector 22 and the energy analyzing crystal 10 properly aligned. This may be automatically accomplished in a number of different ways. One way illustrated in FIG. 1 is to provide guiding slide rods 31 and 32 which are pivotally supported at one end directly below the center of the energy analyzing crystal 16, and at their other ends by the arms 12 and 13 through sleeves 33 and 34 rigidly attached to the platforms 17 and 23 supporting the sample 16 and detector 22, as shown in FIGS. 2 and 3. These guiding slide rods thus turn the platforms as the sleeves slide on the rods to maintain the optical axes of elements on the platforms parallel to the axes of the rods, which in turn have their axis intersecting directly below the center of the energy analyzing crystal 10.

Figure 4:
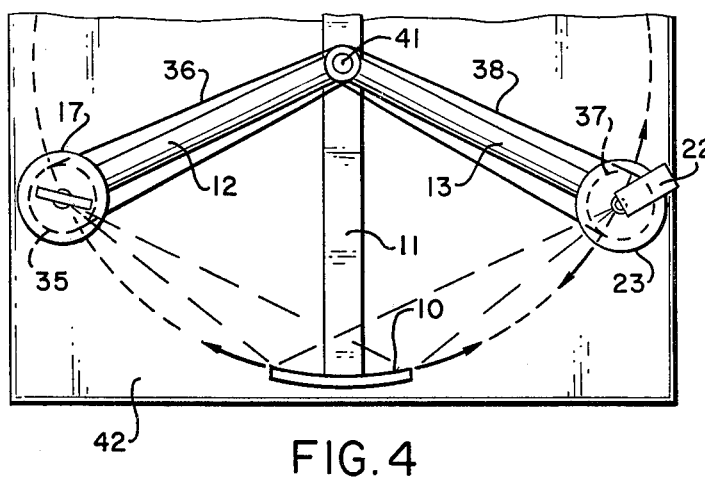
FIG. 4 illustrates schematically a second embodiment of the invention.
Figure 7:
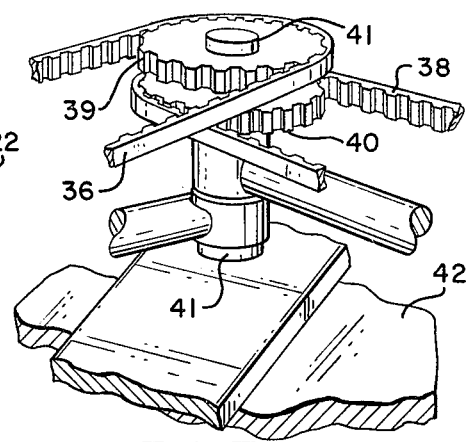
FIG. 7 illustrates details of construction at the pivot point of the two side arms in the embodiment of FIG. 4.
Figure 5:
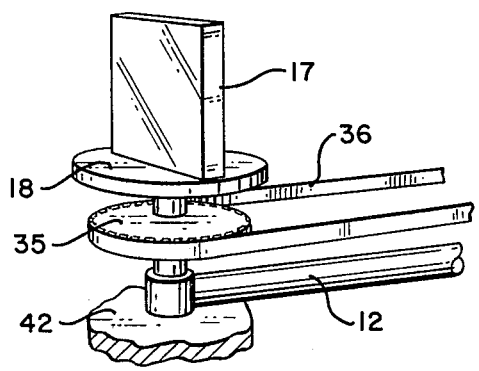
FIG. 5 illustrates details of construction at one end of a side arm in the embodiment of FIG. 4.
Figure 6:
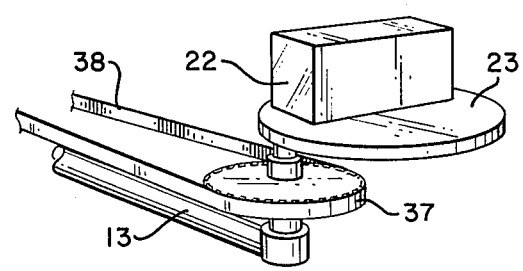
FIG. 6 illustrates details of construction at the other end of a side arm in the embodiment of FIG. 4.

This direct way of maintaining proper alignment has the advantage of simplicity, but the disadvantage of having to provide sleeves that will slide with very little friction and with a fit of high precision. To overcome that disadvantage, it is preferred to omit the guiding slide bars and provide instead belts and pulleys which will turn the platforms through a change in angle equal to twice the change in angle between the central arm 11 and the side arms 12 and 13, as shown in FIG. 4. FIG. 5 shows a pulley 35 for the platform 18 at the end of the arm 12 and a belt 36, and FIG. 6 shows a pulley 37 for the platform 23 at the end of the arm 13 and a belt 38. The belts 36 and 38 pass over pulleys 39 and 40 at the center, as shown in FIG. 7. The pulley 39 is keyed to a shaft 41 which turns with the central arm 11, while the arm 12 is held fixed in space, thereby turning the platform pulley 35 in the same direction, but at half the angular rate because the pulley 35 is twice the diameter of the pulley 39. The pulley 40 is also keyed to the shaft 41 so that, as the arm 11 turns the shaft 41 (which functions as the pivot 24 in FIG. 1), the pulley 40 turns, thereby causing the belt 38 to turn the pulley 37 at the end of the arm 13. The diameter of the pulley 40 is half the diameter of the pulley 37 so the platform 23 is turned through half the angle the arm 13 is turned relative to the central arm 11.

In both embodiments, the central pivot 24 and the end of the arm 12 are rigidly supported by a table 42, while the arms 11 and 13 are free to turn on the pivot 26 in FIG. 1 and the shaft 41 in FIG. 4. It should therefore be evident that, in practice, the arm 12 may be integrated with the table 42. Reference to the arm 12 as a separate entity is for convenience in the description and understanding of the invention. It should also be evident that either the central arm or the other side arm may be rigidly supported by the table, in which case the table itself would serve the function of that rigidly supported arm. If in the embodiment of FIG. 1 that arm is the central arm 11, the slot 30 for the sliding bar 29 would then be in the table and the analyzing crystal 10 would be supported directly on the table. In that case the guide rods 31 and 32 would function just as before, and in the embodiment of FIG. 4, the pulleys 39 and 40 would also function as before. The only difference then being that the pulleys would be keyed to turn with one or the other of the arms 12 and 13, whichever is driven while sweeping the angle $\theta$. The arrangement for maintaining the arm 12 stationary is preferred only because of the preference of keeping the X-ray source 19 and monochromating crystal 20 stationary while only pivoting the sample 16 and mounting plate 18.

The arms 11 and 13 are sufficiently rigid to permit them to be supported only at the pivot. By adding sufficient weight at the end of the arm 11 beyond the crystal 10, to counterbalance the weight of the bars 14, 15 and block 29, the arm 11 can be very nearly balanced about the pivot.

In the preferred arrangement of FIG. 4, the belts are provided with teeth that mesh with teeth in the pulleys, as shown. This is a widely practiced technique which is known to be as precise as the shaft and stepping motor (not shown in FIG. 4) for positioning the arms, so that none of the precision of the shaft and stepping motor is lost by replacing the constraining bars 14 and 15 with the belts and pulleys. In that regard, it should be appreciated that FIG. 4 is a schematic drawing which illustrates this substitution. All of the remaining parts of the embodiment of FIG. 1 remain the same, although not shown in FIG. 4.

As noted hereinbefore, FIG. 1 illustrates the energy analyzer comprised of the three arms 11, 12 and 13, and the energy analyzing crystal 10, in an arrangement for a Raman type experiment using the monochromating crystal 20 to select one of the characteristic lines from the X-ray source 19. Once the selection is made by adjusting the angle of incidence, the source and monochromating crystal are fixed relative to the arm, and the energy analyzer sweeps in energies for Raman fine structure by varying the angle between the central arm and the side arm. For anomalous dispersion, or temperature dependent scattering experiments, the angle of incidence is swept by turning the plate 18 to select different characteristic lines from the X-ray source, and the analyzer is tuned to energy of the successively selected lines from the X-ray source.

Figure 8:
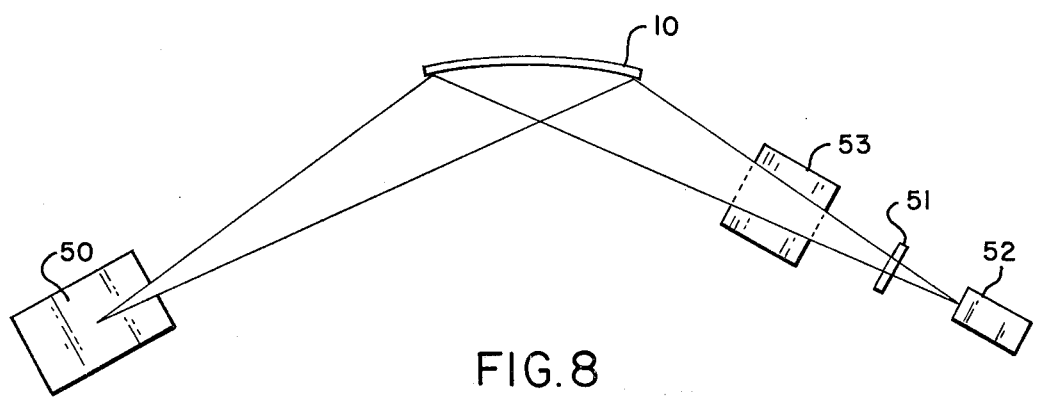
FIG. 8 illustrates schematically use of the present invention for direct EXAFS experiments.

For EXAFS studies, an arrangement is used as shown schematically in FIG. 8, a tungsten anode is used to provide a source 50 of white X-rays. An absorbing sample 51 is placed in front of a detector 52. As before, the arms (not shown) carrying the elements, including the energy analyzing crystal 10, are adjusted with a single movement to sweep the energy analyzer through energies up to about 1 KeV above K-absorption edge of absorbing atom. An ionization chamber 53 in front of the sample measures the intensity of the incident beam, $I_o(E)$, while the detector 52 measures the intensity, $I_t(E)$, of energy transmitted through the sample. The normalized measured energy, $X(E)$ is then given by the following equation:

$$X(E) = [I_o(E) - I_t(E)]/I_o(E)$$

Figure 9:
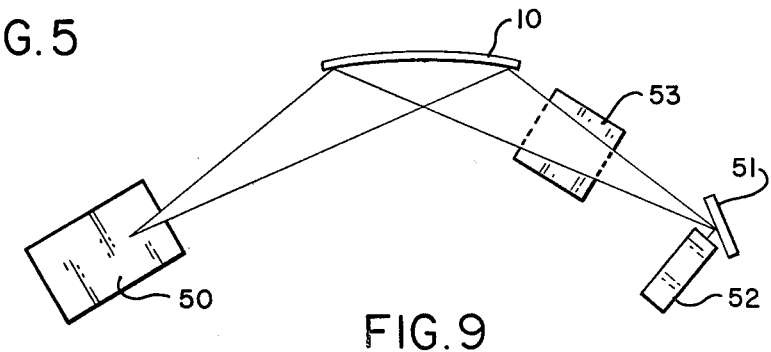
FIG. 9 illustrates schematically use of the present invention for fluorescent EXAFS experiments.

An arrangement for fluorescence EXAFS studies shown in FIG. 9 is essentially the same as that shown in FIG. 8, except that the sample 51 and the detector 52 are positioned to allow incident radiation on the sample, and detection of subsequent fluorescent X-rays from the sample. Photoionization of K-electrons in the sample due to absorption of X-rays will produce the fluorescent X-rays which are measured by the detector placed very close to the sample. The energy analyzer sweeps through energies up to $\sim$1000 eV above the K-absorption edge of absorbing atoms while normalized energy is measured using an equation similar to that above.

Figure 10:
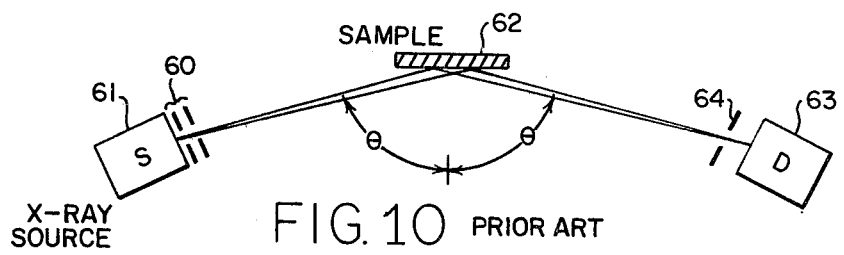
FIG. 10 illustrates a conventional X-ray diffraction experiment using a Bragg-Brentano parafocusing geometry.

Still other applications are made possible by replacing one of the focusing crystals by a homogeneous isotropic sample (i.e., a nonoriented polycrystalline or amorphous material) bent to the radius of the spectrometer. The spectrometer movement is then used as a focusing geometry diffractometer since diffraction from the bent sample always occurs at some well defined diffraction angle, $2\theta$. To understand an example of the usefulness of this geometry, consider a conventional X-ray diffraction experiment shown schematically in FIG. 10 using a Bragg-Brentano parafocusing geometry. A pair of collimating slits 60 (approximately 1°) are placed in front of an X-ray source 61 to provide a collimated beam that is reflected from a sample 62. A detector 63 receives the reflected beam through a slit 64 (typically between 0.2 and 0.01).

The angular resolution of this arrangement for X-ray diffraction experiments is limited usually by the size of the receiving slit, and the intensity of the beam which is small since only a small solid angle of the radiation from the source is utilized. The apparatus of FIG. 1 or FIG. 2 may be utilized for X-ray diffraction experiments by replacing the focusing crystal 10 with a sample bent to conform to the curvature of the replaced crystal. This may be easily accomplished by forming a foil of the sample on the face of a focusing crystal, or a mold having the same shape. This is shown schematically in FIG. 11 where, for convenience, only a sample 65 is shown bent to the shape of a focusing crystal. An X-ray source 66 is then utilized without slits in order to direct all of the energy of the beam onto the sample. A detector 67 is used with a slit 68 which eliminates air scattered and fluorescent X-rays from the detector, and passes into the detector only the focused beam. The diffraction angle is still well resolved in this geometry and a much larger solid angle of radiation may be used. For amorphous materials especially, where the diffraction of X-rays (and neutrons and electrons) is an inefficient process, and intensities are always small, this can be a big advantage. For example, a complete scan of diffracted intensity from $2\theta = 6°$ to 160° on an amorphous metallic alloy typically requires about one week using a 0.3° receiving slit. In the focusing geometry of the present invention which utilizes about 9° of the radiation, the acquisition time can be cut by a factor of 30 (about 6 hours) with the same source with no sacrifice of resolution.

Figure 12:
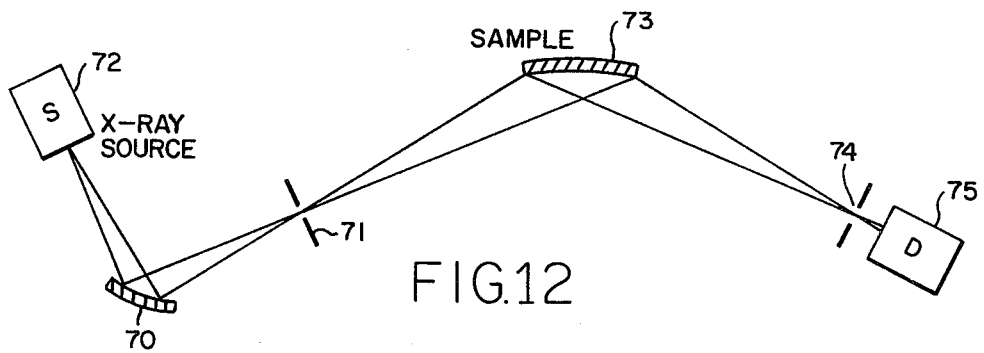
FIG. 12 illustrates a variant of the experiment of FIG. 11 in which an arrangement is used to select X-ray line from the source.

By using either of the two focusing crystals 10 and 20, more elaborate arrangements are possible in which the incident or diffracted beams may be monochromated. For example, in the arrangement shown in FIG. 12, a small focusing crystal 70 is used with a scatter slit 71 to select one of the characteristic X-ray lines of a source 72. The beam is then reflected from a focusing sample 73 to a receiving slit 74 and detector 75. This arrangement is ideal for high acquisition rate X-ray diffraction experiments on amorphous materials. The small focusing crystal 70 would be mounted and adjusted to select, for example, Mo K$\alpha$ radiation and K ($=(4\pi \sin \theta)/\lambda$) would be scanned linearly on the focusing smple 73. Since the drive is linear in $\sin \theta$ (rather than $2\theta$) the value of K would be simply $K = (4\pi/\lambda)(x/2R)$ where x is the distance between the sample and detector.

The roles of the crystal 70 and sample 73 can be reversed by making a small focusing sample and using a large focusing crystal. This setup would not so easily facilitate scanning the diffraction angle from the sample without some further adaptation, but would be useful for measuring inelastic scattering by setting up the sample to diffract at some fixed angle and energy analyzing the scattered radiation to observe, for example, Compton profiles, plasmon scattering or Raman scattering events.

Figure 11:
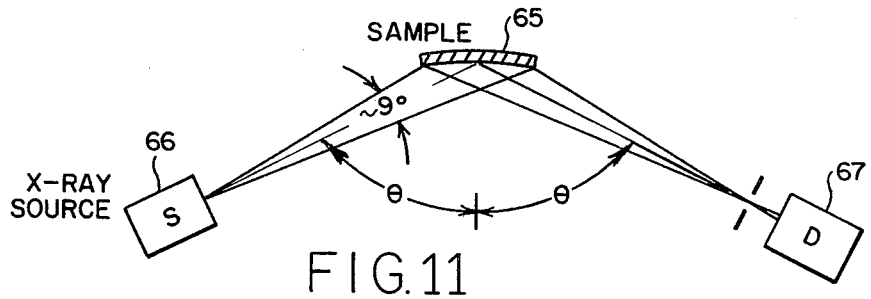
FIG. 11 illustrates the X-ray diffraction experiment of FIG. 10 using the focusing geometry of the present invention.
Figure 13:
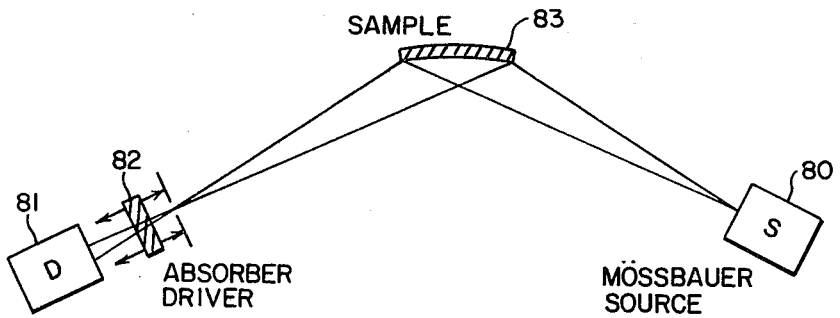
FIG. 13 illustrates an arrangement for Rayleigh scattering experiments.

Another arrangement shown in FIG. 13 consists of replacing the detector and receiving slit in FIG. 11 with a Mossbauer source 80 and slit 81, and replacing the X-ray detector by a gamma ray detector 81 and a matched absorber and driver 82 which can be driven at a high speed to oscillate the position of the absorber in the beam path. A focusing sample 83 does not necessarily have a Mössbauer isotope. In the implementation of this arrangement, the source is placed on the outer arm 13, and the detector is placed on the stationary arm 12 of the apparatus shown in FIG. 1.

The advantage of placing the source on the outer arm 13 is that it is very light and simple, being nothing more than a small length of wire coated with the radioactive isotope. The platform 17, is then used to support the matched absorber connected to an electromechanical drive, lead shields and a detector. When the absorber is at rest, gamma rays from the source which are Rayleigh scattered (elastic) from the sample will be absorbed strongly in the absorber, and only inelastically scattered gamma rays will reach the detector. When the absorber is oscillated at high speed, all the scattered $\gamma$ rays can reach the detector since the Doppler shift produced causes the absorber to be far from the nuclear absorption resonance. In this way the recoil free fraction, $f_s$, of the sample can be obtained as a function of K. The recoil free fraction represents the ratio of completely elastic (Rayleigh) scattering events to the total scattering cross section (elastic plus inelastic) from which values of atomic vibration amplitudes and effective Debye temperatures can be obtained by measuring the angular dependence of f. The conventional arrangement for performing these types of experiments is again through the use of slit collimation and a very strong source ($\sim$100 milliCuries). The focusing geometry of the present invention can be utilized for measurements performed with much higher acqusition rates and with weaker sources.

Although particular embodiments of the invention have been described and illustrated herein, it is recognized that modifications and variations may readily occur to those skilled in the art. Consequently, it is intended that the claims be interpreted to cover such modifications and equivalents.

What is claimed is:

1. A focusing radiation analyzer comprising
   a concave element shaped so that its concave reflecting surface lies on the circumference of a circle,
   means for supporting said concave element on said circumference of a circle,
   two side arms pivoted at the center of said circle, one on each side of said concave element,
   means carried by one side arm for directing radiation from a virtual point source on said circle to said concave element, with its beam axis intersecting the center of said concave element,
   means carried by the other side arm for receiving at a point on said circle radiation from said concave element, with its beam axis intersecting the center of said concave element,
   means for maintaining arcs on said circle between the center of said concave element and each side arm equal as the arc of one side arm is varied, and
   means for simultaneously maintaining the beam axis of said radiation means and the beam axis of said receiving means intersecting the center of said concave element as said arc of one side arm is varied, wherein said concave element is a diffraction sample bent for focusing radiation from said virtual point source on said circle to said receiving point of the receiving means on said circle.

2. A focusing radiation analyzer as defined in claim 1, wherein said point source is an X-ray source and said receiving means is an X-ray detector with a slit, said slit being positioned at said receiving point.

3. A focusing radiation analyzer as defined in claim 2 wherein said radiation source includes an X-ray source, a slit, and a concave reflecting element shaped so that its concave reflecting surface focuses radiation from said X-ray source to said slit to select a characteristic X-ray line of said X-ray source.

4. A focusing radiation analyzer comprising
   a concave element shaped so that its concave reflecting surface lies on the circumference of a circle,
   means for supporting said concave element on said circumference of a circle,
   two side arms pivoted at the center of said circle, one on each side of said concave element,
   means carried by one side arm for directing a radiation beam from a virtual point source on said circle to said concave element, with its beam axis intersecting the center of said concave element, said means including a sample, and said virtual point source is on the face of said sample, said sample being positioned to reflect a radiation beam to said concave element, said means further including means for generating an X-ray beam and means for focusing said X-ray beam onto said point on the face of said sample for reflection to said concave element,
   means carried by the other side arm for receiving at a point on said circle radiation from said concave element, with its beam axis intersecting the center of said concave element,
   means for maintaining arcs on said circle between the center of said concave element and both of said side arms equal as the arc between one side arm and the center of said concave element is varied, and
   means for simultaneously maintaining the beam axis of said radiation means and the axis of said receiving means intersecting the center of said concave element as the arcs between said side arms and the center of said concave element are varied equally.

5. A focusing radiation analyzer as defined in claim 4 wherein said means for focusing said X-ray beam onto said point on the face of said sample is comprised of a concave element shaped so that its concave reflecting surface lies on the circumference of a second circle passing through said point on the face of said sample for focusing radiation from said beam generating means to said point on the face of said sample, said beam generating means and concave element being adjustable in position relative to the face of said sample for selecting a characteristic line of said X-ray source.

6. A focusing radiation analyzer comprising a concave element shaped so that its concave reflecting surface lies on the circumference of a circle,
means for supporting said concave element on said circumference of a circle,
two side arms pivoted at the center of said circle, one on each side of said concave element,
means carried by one side arm for directing radiation from a virtual point source on said circle to said concave element, with its beam axis intersecting the center of said concave element,
means carried by the other side arm for receiving at a point on said circle radiation from said concave element, with its beam axis intersecting the center of said concave element,
means for maintaining arcs on said circle between the center of said concave element and each side arm equal as the arc between one side arm and the center of said concave element is varied,
means for simultaneously maintaining the beam axis of said radiation means and the beam axis of said receiving means intersecting the center of said concave element as the arc between one side arm and the center of said concave element is varied, and
wherein said point source is an X-ray source and said receiving means includes a sample and an X-ray radiation detector and said receiving point is on the face of said sample, said sample being positioned to reflect said radiation beam from said concave element into said detector.

7. A focusing radiation analyzer as defined in claim 6 including means for measurement of the intensity of the beam from said concave element to said sample.

8. A focusing radiation analyzer comprising
a concave element shaped so that its concave reflecting surface lies on the circumference of a circle,
means for supporting said concave element on said circumference of a circle,
two side arms pivoted at the center of said circle, one on each side of said concave element,
means carried by one side arm for directing radiation from a virtual point source on said circle to said concave element, with its beam axis intersecting the center of said concave element,
means carried by the other side arm for receiving at a point on said circle radiation from said concave element, with its beam axis intersecting the center of said concave element,
means for maintaining arcs on said circles between the center of said concave element and each side arm equal as the arc of one side arm is varied, and
means for simultaneously maintaining the beam axis of said radiation means and the beam axis of said receiving means intersecting the center of said concave element as said arc of one side arm is varied, wherein said point source is an X-ray source and said receiving means is an X-ray radiation detector, and wherein a sample is placed in the path of the beam from said concave element to said detector.

9. A focusing radiation analyzer as defined in claim 8 including means for measurement of the intensity of the beam from said concave element to said sample.

10. A focusing radiation analyzer comprising
a concave element shaped so that its concave reflecting surface lies on the circumference of a circle,
means for supporting said concave element on said circumference of a circle,
two side arms pivoted at the center of said circle, one on each side of said concave element,
means carried by one side arm for directing radiation from a virtual point source on said circle to said concave element, with its beam axis intersecting the center of said concave element,
means carried by the other side arm for receiving at a point on said circle radiation from said concave element, with its beam axis intersecting the center of said concave element,
means for maintaining arcs on said circle between the center of said concave element and each side arm equal as the arc of one side arm is varied, and
means for simultaneously maintaining the beam axis of said radiation means and the beam axis of said receiving means intersecting the center of said concave element as the arc of one side arm is varied, wherein said source is a Mossbauer source, said receiving means is a gamma ray detector with a slit, said slit being positioned at said receiving point, and said concave element is a sample bent for focusing radiation from said virtual point source on said circle to said receiving point of the receiving means on said circle.

11. A focusing radiation analyzer comprising
a concave focusing element shaped so that its concave reflecting surface lies on the circumference of a circle,
means on the circumference of said circle for providing a beam of radiant energy with its axis intersecting the center of said element,
means on the circumference of said circle for detecting radiant energy, said detecting means having its optical axis intersecting the center of said element,
two pivotal arms for positioning said beam providing means and said detector means on opposite sides of said focusing element, said arms being pivoted at the center of said circle,
means for moving one arm to adjust the position between said focusing element and said one arm for a selected angle,
means for moving the other arm in response to movement of the one arm to adjust the position between said focusing element and said other arm for the angle selected for said one arm, and
means responsive to the movement of said one arm and said other arm for adjusting the angular position of said beam providing means and said detector means to maintain the axis of said beam of radiation intersecting the center of said focusing element and the optical axis of said detecting means intersecting the center of said focusing element for any selected angle comprised of a first sliding guide rod and a second sliding guide rod, said first and second rods being positioned at a point directly below the center of said focusing element, and two sleeves, one sleeve around each one of said rods, one sleeve rigidly connected to said beam providing means in a position with its axis directly below the pivotal center of said beam providing means the the other sleeve rigidly connected to detector means in a position with its axis directly below the pivotal center of said detector means.

12. A focusing radiation analyzer comprising
a concave focusing element shaped so that its concave reflecting surface lies on the circumference of a circle, means on the circumference of said circle for providing a beam of radiant energy with its axis intersecting the center of said element, means on the circumference of said circle for detecting radiant energy, said detecting means having its optical axis intersecting the center of said element, two pivotal arms for positioning said beam providing means and said detector means on either side of said focusing element, said arms being pivoted at the center of said circle, means for moving one arm to adjust the position between said focusing element and said one arm for a selected angle, means for moving the other arm in response to movement of the one arm to adjust the position between said focusing element and said other arm for the angle selected for said one arm, and means responsive to the movement of said one arm and said other arm for adjusting the angular position of said beam providing means and said detector means to maintain the axis of said beam of radiation intersecting the center of said focusing element and the optical axis of said detecting means intersecting the center of said focusing element for any selected angle comprised of two belts and two pulleys for each belt, one pulley for one belt being rigidly connected to said beam providing means, one pulley for the other belt being rigidly connected to said detector means, and the other pulley of both belts being half the diameter of the one pulley, and both of said other pulleys being rigidly fixed relative to said focusing element with their axis passing through the center of said circle, whereby movement of said pivotal arms relative to said focusing element through a selected angle produces pivotal movement of said beam providing means and said detector means through half their angles to maintain the axes of said beam and said detector intersecting the center of said focusing element.

* * * * *